United States Patent
Kelly et al.

(10) Patent No.: US 9,248,077 B1
(45) Date of Patent: Feb. 2, 2016

(54) COMPLETELY CLOSED SYRINGE SYSTEM

(71) Applicants: Patricia A. Kelly, Burbank, CA (US);
Joan P. Ortiz, Burbank, CA (US); Leslie Beckwith, La Mirada, CA (US)

(72) Inventors: Patricia A. Kelly, Burbank, CA (US);
Joan P. Ortiz, Burbank, CA (US); Leslie Beckwith, La Mirada, CA (US)

(73) Assignee: LIMERICK, INC., Burbank, CA (US)

( * ) Notice: Subject to any disclaimer, the term of this patent is extended or adjusted under 35 U.S.C. 154(b) by 0 days.

(21) Appl. No.: 14/336,124

(22) Filed: Jul. 21, 2014

Related U.S. Application Data

(60) Provisional application No. 61/856,179, filed on Jul. 19, 2013, provisional application No. 61/857,316, filed on Jul. 23, 2013.

(51) Int. Cl.
| | |
|---|---|
| *A61J 1/16* | (2006.01) |
| *A61M 1/06* | (2006.01) |
| *A61J 9/06* | (2006.01) |
| *A61J 9/00* | (2006.01) |
| *B65D 83/00* | (2006.01) |
| *A61M 1/00* | (2006.01) |

(52) U.S. Cl.
CPC . *A61J 1/16* (2013.01); *A61M 1/062* (2014.02); *A61J 9/00* (2013.01); *A61J 9/06* (2013.01); *A61M 1/0001* (2013.01); *A61M 1/06* (2013.01); *B65D 83/0005* (2013.01)

(58) Field of Classification Search
CPC ..... A61M 1/0001; A61M 1/06; A61M 1/062; A61M 1/0017; A61J 9/00; A61J 9/003; A61J 9/06; A61J 9/08; A61J 9/085; A61J 2009/0615; B65D 83/0005; B65D 47/08; B65D 47/2031

USPC ..................................................... 604/74–76
See application file for complete search history.

(56) References Cited

U.S. PATENT DOCUMENTS

| | | | | |
|---|---|---|---|---|
| 2,066,445 | A | * | 1/1937 | Allen ........................... 215/11.5 |
| 4,772,273 | A | * | 9/1988 | Alchas .......................... 604/218 |
| 4,821,896 | A | * | 4/1989 | Cheng .......................... 215/11.3 |
| 5,749,850 | A | * | 5/1998 | Williams et al. ................ 604/74 |
| 6,616,000 | B1 | * | 9/2003 | Renz ............................ 215/11.1 |
| 7,833,190 | B1 | * | 11/2010 | Hall ................................. 604/74 |
| 2004/0122356 | A1 | * | 6/2004 | Burke et al. .................... 604/74 |
| 2005/0284835 | A1 | * | 12/2005 | McKendry et al. ........... 215/11.1 |
| 2006/0025718 | A1 | * | 2/2006 | Ostrowski ....................... 604/74 |
| 2010/0022984 | A1 | * | 1/2010 | Knight .......................... 604/403 |
| 2011/0151069 | A1 | * | 6/2011 | Harding ........................ 426/117 |
| 2012/0065608 | A1 | * | 3/2012 | Costello et al. ............... 604/403 |
| 2012/0265169 | A1 | * | 10/2012 | Sherman et al. ............... 604/514 |
| 2013/0030379 | A1 | * | 1/2013 | Ingram et al. ................. 604/218 |
| 2013/0281983 | A1 | * | 10/2013 | Sherman et al. .............. 604/514 |
| 2014/0052106 | A1 | | 2/2014 | Sherman |

* cited by examiner

*Primary Examiner* — Andrew Gilbert
(74) *Attorney, Agent, or Firm* — Kenneth L. Green; Averill & Green

(57) ABSTRACT

A cap and rigid bottle converts an expressed milk syringe from an open system to a closed system. The cap is in fluid communication between a breast pump and breast cup. The rigid bottle is attached to the bottom of the cap and the syringe is captured inside the bottom under the cap in a sealed environment. The pump provides varying positive vacuum to the cap and through the cap to the breast cup. Milk is drawn by the vacuum into the cap and flows by gravity down into the syringe. A passage between the interior of the syringe and the interior of the bottle equalizes pressure and allows the syringe to fill while maintaining a closed system, allowing a piston in the syringe to remain stationary. The closed system protects a mother's milk being pumped into a milk collecting syringe from air born contaminants.

20 Claims, 3 Drawing Sheets

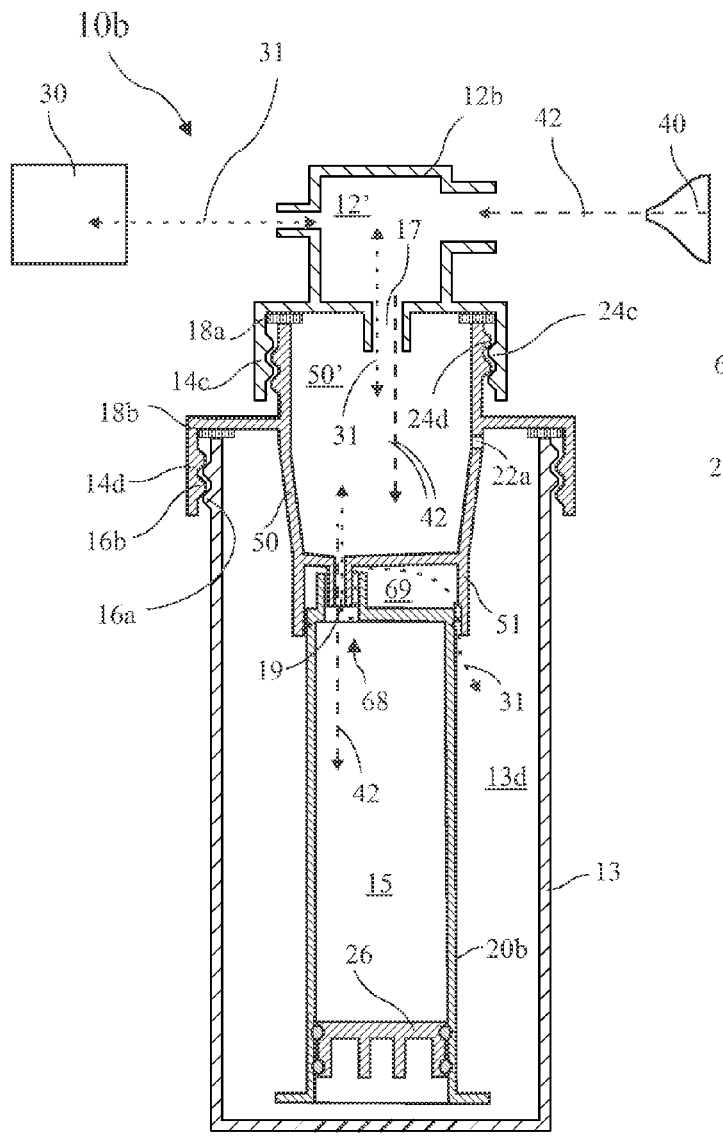
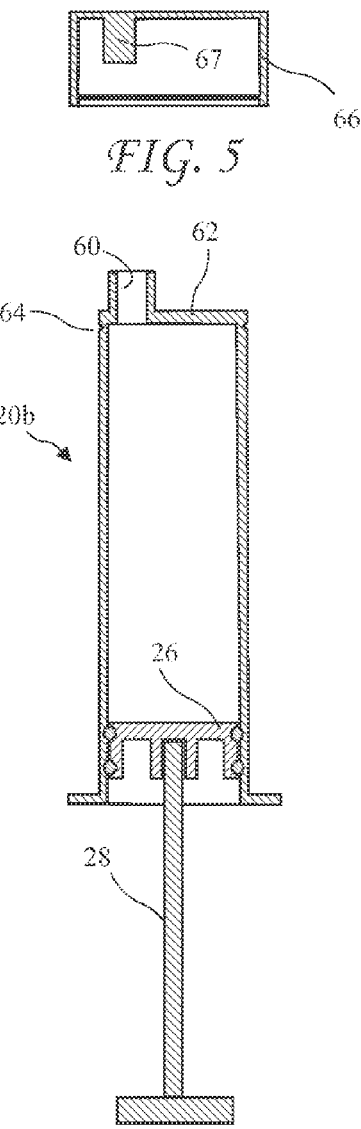
FIG. 3
FIG. 4
FIG. 5

COMPLETELY CLOSED SYRINGE SYSTEM

CROSS-REFERENCE TO RELATED APPLICATIONS

The present application claims the priority of U.S. Provisional Patent Application Ser. No. 61/856,179 filed Jul. 19, 2013 and of U.S. Provisional Patent Application Ser. No. 61/857,316 filed Jul. 23, 2013, which applications are incorporated in their entirety herein by reference.

BACKGROUND OF THE INVENTION

The present invention relates to breast pumps and in particular to a completely closed syringe system to protect a mother's expressed milk from contamination.

The syringe is used to feed the mother's milk to her sick baby in Neonatal Intensive Care Units (NICU). Currently, the milk is collected and stored in an open syringe for feeding babies in the NICU. The milk is not protected from air born contaminants.

Known electric breast pump systems include a special bottle cap which fits a standard baby bottle for collecting milk. The special bottle cap is used to connect the bottle between the electric breast pump and a breast cup. The various electric breast pump system models use their own special cap to work with their pump system. These known electric breast pump systems do not allow directly filling a syringe for use in NICUs.

BRIEF SUMMARY OF THE INVENTION

The present invention addresses the above and other needs by providing a cap and rigid bottle converts an expressed milk syringe from an open system to a closed system. The cap is in fluid communication between a breast pump and breast cup. The rigid bottle is attached to the bottom of the cap and the syringe is captured inside the bottom under the cap in a sealed environment. The pump provides varying positive vacuum to the cap and through the cap to the breast cup. Milk is drawn by the vacuum into the cap and flows by gravity down into the syringe. A passage between the interior of the syringe and the interior of the bottle equalizes pressure and allows the syringe to fill while maintaining a closed system, allowing a piston in the syringe to remain stationary. The closed system protects a mother's milk being pumped into a milk collecting syringe from air born contaminants.

In accordance with one aspect of the invention, there is provided a completely enclosed system for collecting mother's milk into the syringe while preventing air borne contaminants for reaching the milk.

In accordance with another aspect of the invention, there is provided an adapter bottle to enclose the syringe. The syringe is sealed inside the bottle and pressure is equalized between the syringe and the bottle, allowing continued filling and allowing a piston in the syringe to remain stationary.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 3 shows a cross-sectional view of a second breast pump system according to the present invention.

FIG. 4 shows a cross-sectional view of a second syringe of the second breast pump system according to the present invention.

FIG. 5 shows a cross-sectional view of a cap for the second syringe of the second breast pump system according to the present invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figure 1:
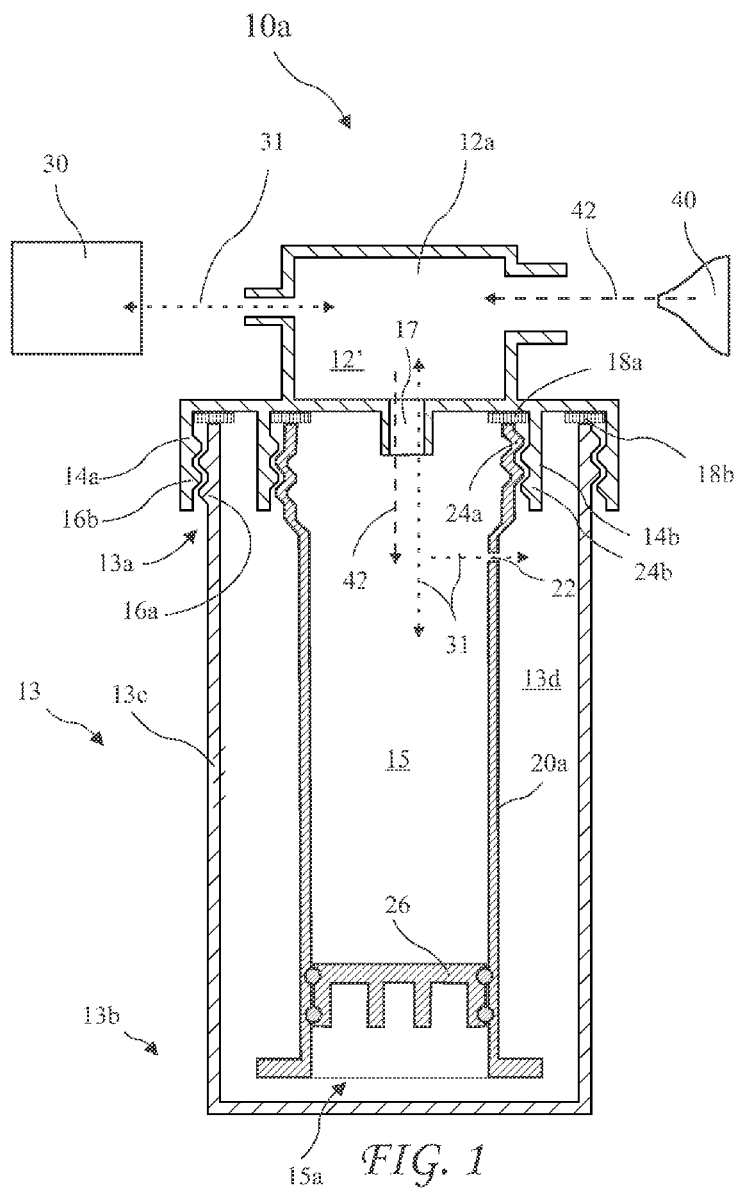
FIG. 1 shows a first breast pump system according to the present invention.
Figure 2:
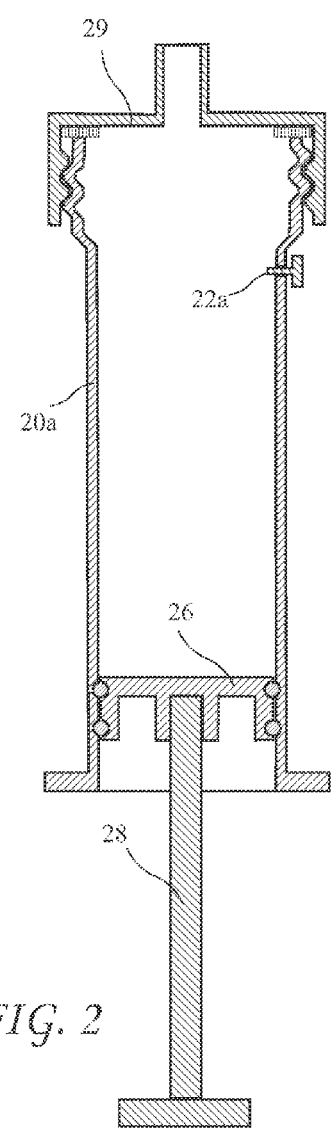
FIG. 2 shows a cross-sectional view of a first syringe of the first breast pump system according to the present invention.

A cross-sectional view of a first closed breast pump system 10a according to the present invention is shown in FIG. 1 and a cross-sectional view of a first syringe 20a having a syringe interior 15 and open syringe base 15a is shown in FIG. 2. The breast pump system 10a includes a first cap 12a, a bottle 13, a first syringe 20a, a pump 30, and a breast cup 40. The bottle 13 is preferably clear plastic with a cylindrical shape and of a size sufficient to enclose the syringe 20a. The bottle 13 includes an open end 13a including male threads 16a, and closed walls 13c and a closed end 13b. The bottle 13 is preferably hard plastic and can withstand a vacuum level of at least 400 mm Hg without deformation or damage. The cap 12a is similar to a standard baby bottle cap but includes an outer rim 14a including female threads 16b which cooperate with the threads 16a to attach the cap 12a to the bottle 13 and an open passage 17 placing the syringe interior 15 in fluid communication with the cap interior 12'. A silicone rubber washer 18b is preferably included to ensure an airtight seal when the cap 12a and bottle 13 are fully threaded together.

The syringe device 20a includes a syringe mating surface (e.g., male threads) 24a and the cap 12a includes an inner rim 14b having a cap mating surface (e.g. female threads) 24b cooperating with the male threads 24a to connect the syringe 20a to the cap 12a. A second silicone rubber washer 18a may be included between the syringe 20a and the cap 12a, and a closing device (for example, a piston 26) resides in or under the base of the syringe 20a. The cap 12a is connected to the pump 30 and to the breast cup 40. A cyclic air flow 31 between the pump 30 and the cap 12a varies a vacuum level in the cap 12a between a lower and a higher positive vacuum, and maintains at least some level of positive vacuum at all times in the cap 12a, for example, to prevent the breast cup 40 from falling away. The vacuum levels are maintained regardless of the size of the syringe 20a or the amount of milk 42 inside the syringe 20a. The vacuum is drawn from the cap 12a, the syringe 20a, interior 13d of the bottle 13 through the vent 22, and the breast cup 40 by the pump 30. The vacuum draws milk 42 from the breast cup 40 into a cap interior 12' of the cap 12a. The milk 42 then falls by gravity from the cap interior 12' into the syringe 20a. Because the vent 22 maintains equal vacuum in the syringe 20a and the bottle interior 13a, the vacuum level is the same both inside and outside the syringe 20a and there is no force on the piston 26. If there were no vent 22, the piston 26 would tend to move upward under vacuum, gradually rising in the syringe 20a.

Those skilled in the art will recognize that the vent 22 is only one example of a passage equalizing the vacuum level in the syringe 20a and bottle 13, and other passages may be provided and are intended to come within the scope of the present invention.

The bottle interior 13a and the syringe interior 15 are in fluid communication to allow air within the syringe 20a to escape as it fills with breast milk. The fluid communication may, for example, be provided through a vent 22 in the syringe 20a, or may be through direct fluid communication between the cap and bottle. The venting prevents a vacuum gradient from developing between the syringe 20a and the bottle 13 and the adapter bottle 13 provides an air tight enclosure containing the syringe 20 to allow vacuum build-up within the adapter bottle 13. Without the adapter bottle 13, the air drawn from the syringe 20a is immediately replaced by air entering the vent, and no significant vacuum is created, and air borne contaminant may enter the syringe. Due to the presence of the adapter bottle 13, the air within the adapter bottle 13, the syringe 20a, and the breast cup 40, is drawn by the pump 30, creating vacuum and drawing the milk 42 from the breast cup 40 to fill the syringe 20a After filling the syringe 20a with milk 42, the syringe 20a may be removed from the cap 12a and bottle 13. A handle 28 may be attached to the piston 26, and a feeding cap 29 attached to the male threads 24a for use. A plug 22a is inserted into the vent 22 to seal the syringe 20a.

A cross-sectional view of a second closed breast pump system 10b according to the present invention is shown in FIG. 3. The closed breast pump system 10b functions in the same manner as the closed breast pump system 10a, but includes an adapter 50 (also see FIGS. 6A, 6B, and 6C) between a second cap 12b, and the bottle 13 and second syringe 20b. The breast pump system 10b includes the pump 30 and the breast cup 40 connected to the bottle cap 12b, the adapter 50, the syringe 20b, and the bottle 13. The cap 12b is similar to known baby bottle caps and preferably includes a downward reaching rim 14c having female threads 24c which cooperate with threads 24d of the adapter 50. The threads 24c are preferably comparable with standard baby bottle threads. A first silicone rubber washer 18a preferably resides between the bottle cap 12 and adapter 50 and ensures an airtight seal when the cap 12b and adapter 50 are fully threaded together.

The adapter 50 includes an outer downward extending rim 14d having female threads 16b which engage the threads 16a on the bottle 13. A second silicone rubber washer 18b preferably resides between the adapter 50 and hard bottle 13 and ensures an airtight seal when the adapter 50 and bottle 13 are fully threaded together.

The adapter 50 includes an inner downward reaching skirt 51 and the second syringe device 20b engages the downward reaching skirt 51 and resides in the hard outer bottle 13. The cap interior 12' is vented through adapter 50 and the syringe 20b into the bottle interior 13a to allow air to pass and between the interior of the bottle 13 and the syringe 20b during operation of the breast pump system 10b and equalize the vacuum in the syringe 20a and bottle interior 13a. The adapter 50 and hard plastic bottle 13 provides an air tight enclosure outside the syringe 20b to allow equal vacuum build-up within the syringe 20b and hard plastic bottle 13.

A cross-sectional view of the syringe 20b is shown in FIG. 4 and a cross-sectional view of a syringe cap 66 is shown in FIG. 5. The syringe 20b includes a mouth 60 extending up from an otherwise closed end 62. The mouth 60 engages a downward extending nipple 56 (see FIG. 6a) inside the adapter skirt 51 to receive the milk 42 and to allow air to pass between the cap 12b, adapter 50, and syringe 20b. The syringe 20b further includes an annular groove 64 just below the closed end 62 which engages a protrusion 52 (see FIG. 6A) in the adapter skirt 51 to attach the syringe 20b to the adapter 50. The syringe cap 66 may be attached to the syringe 20b and a plug 67 in the cap enter the mouth 60 to seal the syringe 20b.

Figure 6B:
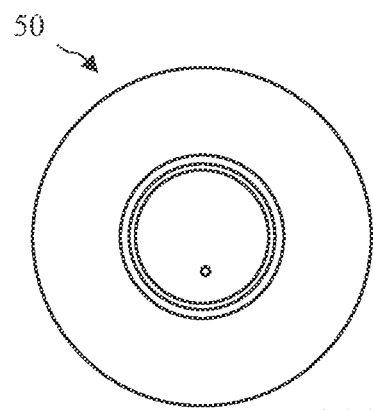
FIG. 6B shows a top view of the adapter of the second breast pump system according to the present invention.
Figure 6A:
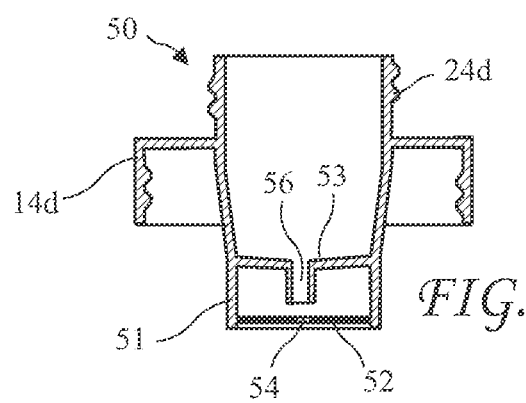
FIG. 6A shows a cross-sectional view of an adapter of the second breast pump system according to the present invention.
Figure 6C:
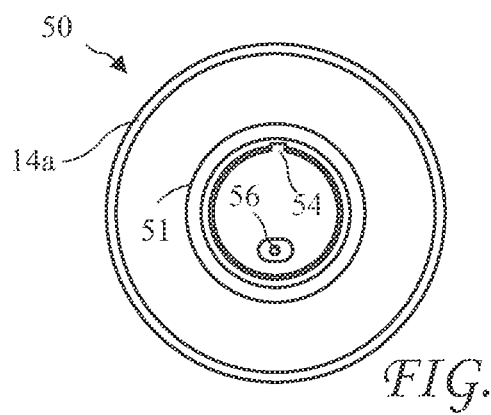
FIG. 6C shows a bottom view of the adapter of the second breast pump system according to the present invention.

A cross-sectional view of the adapter 50 of the breast pump system 10b is shown in FIG. 6A, top view of the adapter 50 is shown in FIG. 6B, and a bottom view of the adapter 50 is shown in FIG. 6C. The adapter 50 includes a floor 53 sloping down to the nipple 56. The nipple 56 reaches into the mouth 60 of the syringe 20d. The protrusion 52 circles the inside of the skirt 51 and the groove 64 on the syringe 20b cooperates with the protrusion to hold the syringe 20b in place.

The cap 12b is ported to the bottle 13 as in the case of the closed breast pump system 10a to similarly eliminate a pressure gradient between the syringe interior 15 and the bottle interior 13a. Such porting may be accomplished by a vent 22 in the syringe 20b as in the syringe 20a, or by other means. For example, a gap 68 may be present between the nipple 56 and mouth 60 porting the syringe interior 15 to a volume 69 between the syringe 20b and the adapter 50, and protrusion 52 and/or skirt 51 may have a notch 54 placing the volume 69 in fluid communication with the bottle interior 13a. Other portings will be obvious to those skilled in the art, and any closed breast pump system including porting to eliminate pressure gradients between the syringe 20b and the bottle 13 are intended to come within the scope of the present invention.

While the invention herein disclosed has been described by means of specific embodiments and applications thereof, numerous modifications and variations could be made thereto by those skilled in the art without departing from the scope of the invention set forth in the claims.

We claim:

1. A cap and bottle to convert an expressed milk syringe from an open system to a closed system, comprising:
    a rigid external unenclosed bottle having a bottle interior defined by an open end, closed walls, and a closed end opposite to the open end, the bottle interior closed to fluid communication through the closed end and the closed walls;
    a cap sealable to the bottle at the open end of the bottle and having a cap interior;
    a syringe residing in the bottle below the cap and having a syringe interior in fluid communication with the cap interior though a passage in the cap, and in fluid communication with the bottle interior, the syringe interior having a same vacuum level as a portion of the bottle interior outside the syringe, and the syringe having an open base, wherein the bottle interior and the syringe interior provide a fixed volume extension of the cap interior separated from communication with ambient air;
    a piston residing in the syringe interior blocking fluid flow from the syringe interior into the bottle interior, equal vacuum on top and bottom surfaces of the piston enabling the piston to remain stationary during use;
    the cap further configured to connect with a vacuum pump in fluid communication with the cap interior creating vacuum in the cap interior; and the cap further configured to connect with a breast cup in fluid communication with the cap interior.

2. The cap and bottle of claim 1, wherein the cap includes first female thread on an inner rim descending from the cap for attaching the syringe and second female threads on an outer rim descending from the cap for attaching the bottle.

3. The cap and bottle of claim 1, further including an adapter connecting the bottle to the cap, wherein;
the cap includes first female thread on an inner rim descending from the cap for sealingly attaching the adapter;
the adapter includes second female thread on an outer rim descending from the adapter for attaching of the bottle; and
the adapter includes an inner mouth descending from the adapter and inside the bottle for attaching the syringe.

4. The cap and bottle of claim 1, wherein the syringe interior is in fluid communication with a portion of the bottle interior outside the syringe interior, through a vent passage in a wall of the syringe, and the bottle is otherwise sealed.

5. The cap and bottle of claim 1, wherein the syringe interior is in fluid communication with the bottle interior through a vent passage in an adapter connecting the syringe to the cap, and the bottle is otherwise sealed.

6. The cap and bottle of claim 1, wherein the bottle interior is in fluid communication with the cap interior through a notch in mating surfaces engaging the syringe, and the bottle is otherwise sealed.

7. The cap and bottle of claim 1, wherein the syringe interior is sealed from fluid communication with volumes other than the bottle interior and the cap interior.

8. The cap and bottle of claim 1, wherein the syringe interior is in exclusive direct fluid communication with the bottle interior and the cap interior.

9. The cap and bottle of claim 1, wherein pressures on opposite sides of the piston are equal.

10. A closed system for capturing milk, comprising:
a breast pump;
a breast cup;
a rigid external unenclosed bottle having a bottle interior, an open top, and closed sides and bottom;
a cap sealed to the open top of the bottle and having a cap interior;
a syringe residing in the bottle below the cap and having a syringe interior in fluid communication with the cap interior and with a portion of the bottle interior outside the syringe interior, the syringe interior having a same vacuum level as the portion of the bottle interior outside the syringe, the syringe interior unexposed to ambient air outside the bottle;
a piston residing in the syringe interior sealing the syringe to block fluid flow from a base of the syringe interior to the bottle interior;
the breast pump in fluid communication with the cap interior creating vacuum in the cap interior; and
the breast cup in fluid communication with the cap interior to provide milk.

11. The cap and bottle of claim 10, wherein the cap includes first female thread on an inner rim descending from the cap for attaching the syringe and second female threads on an outer rim descending from the cap for attaching the bottle.

12. The cap and bottle of claim 10, further including an adapter connecting the bottle to the cap, wherein;
the cap includes first female thread on an inner rim descending from the cap for sealingly attaching the adapter;
the adapter includes second female thread on an outer rim descending from the adapter for attaching of the bottle; and
the adapter includes an inner mouth descending from the adapter and inside the bottle for attaching the syringe.

13. The cap and bottle of claim 10, wherein the syringe interior is in exclusive direct fluid communication with the bottle interior and the cap interior.

14. The cap and bottle of claim 13, wherein the syringe interior is in fluid communication with the bottle interior exclusively through a vent passage in the syringe.

15. The cap and bottle of claim 10, wherein the syringe interior is in exclusive fluid communication with the bottle interior, and with the cap interior through an adapter interior of an adapter connecting the syringe to the cap, and not otherwise in fluid communication.

16. The cap and bottle of claim 15, wherein the bottle interior is in fluid communication with the adapter interior through a vent passage in the adapter.

17. The cap and bottle of claim 15, wherein the bottle interior is in fluid communication with the cap interior through a notch in mating surfaces engaging the syringe.

18. A closed system for capturing milk, comprising:
a hard plastic, external, unenclosed bottle having closed walls and closed bottom and a bottle interior and remaining rigid up to a vacuum level of at least 400 mm Hg;
a cap connected to the bottle and having a cap interior;
a syringe residing in the bottle below the cap and having a syringe interior in fluid communication with the cap interior and with a portion of the bottle interior outside the syringe, and having a same vacuum level as the portion of bottle interior outside the syringe, the syringe interior separated from air borne contaminates by the cap and bottle;
a piston residing in the syringe interior sealing the syringe to block fluid flow from a base of the syringe interior to the portion of bottle interior outside the syringe;
a vacuum pump in fluid communication with the cap interior creating vacuum in the cap interior; and
a breast cup in fluid communication with the cap interior.

19. The cap and bottle of claim 18, wherein the syringe interior is in exclusive fluid communication with a portion of the bottle interior outside the syringe interior and the cap interior.

20. The cap and bottle of claim 18, wherein the syringe interior is in exclusive fluid communication with a portion of the bottle interior outside the syringe and through an adapter interior of an adapter connecting the syringe and to the cap, and not otherwise in fluid communication.

\* \* \* \* \*